(12) United States Patent
Becker

(10) Patent No.: US 10,764,400 B2
(45) Date of Patent: Sep. 1, 2020

(54) SEMANTIC SHARING OF RESOURCES IN A NETWORK OF MEDICAL DEVICES

(71) Applicant: Siemens Healthcare GmbH, Erlangen (DE)

(72) Inventor: Detlef Becker, Moehrendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/200,955

(22) Filed: Nov. 27, 2018

(65) Prior Publication Data

US 2019/0166227 A1  May 30, 2019

(30) Foreign Application Priority Data

Nov. 29, 2017  (EP) .................................... 17204310

(51) Int. Cl.
| | |
|---|---|
| *G06F 15/177* | (2006.01) |
| *H04L 29/08* | (2006.01) |
| *G06F 9/4401* | (2018.01) |
| *G16H 40/20* | (2018.01) |
| *G06F 8/60* | (2018.01) |

(52) U.S. Cl.
CPC ................ *H04L 67/34* (2013.01); *G06F 8/60* (2013.01); *G06F 9/4411* (2013.01); *G16H 40/20* (2018.01); *H04L 67/104* (2013.01); *H04L 67/1061* (2013.01); *H04L 67/1068* (2013.01); *H04L 67/1076* (2013.01); *H04L 67/1078* (2013.01); *H04L 67/12* (2013.01); *H04L 67/16* (2013.01)

(58) Field of Classification Search
USPC .................................. 709/220, 201, 202, 205
See application file for complete search history.

(56) References Cited

U.S. PATENT DOCUMENTS

| | | | | |
|---|---|---|---|---|
| 10,002,235 | B2 * | 6/2018 | Gray | ................... G06F 19/3418 |
| 10,305,869 | B2 * | 5/2019 | Rosenberg | ............. G16H 50/70 |
| 2005/0132221 | A1 * | 6/2005 | Marcjan | ................ H04L 63/101 |
| | | | | 726/4 |
| 2012/0191860 | A1 * | 7/2012 | Traversat | ............... G06F 9/4416 |
| | | | | 709/226 |
| 2013/0204924 | A1 * | 8/2013 | Nair | ..................... G06F 9/45545 |
| | | | | 709/203 |
| 2017/0104818 | A1 * | 4/2017 | Viggers | ................. G06F 17/212 |
| 2017/0124271 | A1 | 5/2017 | Aase et al. | |

OTHER PUBLICATIONS

Extended European Search Report for European Application No. EP17204310 dated May 22, 2018.
Ggarwal Anurag et al: "Licensing Technology": XP055475258.

\* cited by examiner

*Primary Examiner* — Lan Dai T Truong
(74) *Attorney, Agent, or Firm* — Harness, Dickey & Pierce, P.L.C.

(57) ABSTRACT

A resource sharing system is for sharing local computing resources on devices within a medical network. The sharing system including a plurality of distributed devices, registered in the system and interconnected by a network. Each device includes at least one module communicating via a device-specific interface for providing a resource locally on the device. The device is provided with a device-specific service host for providing local resources to remote devices and for accessing foreign resources of at least one remote device. Further, a device, a method and a computer program product are disclosed.

17 Claims, 4 Drawing Sheets

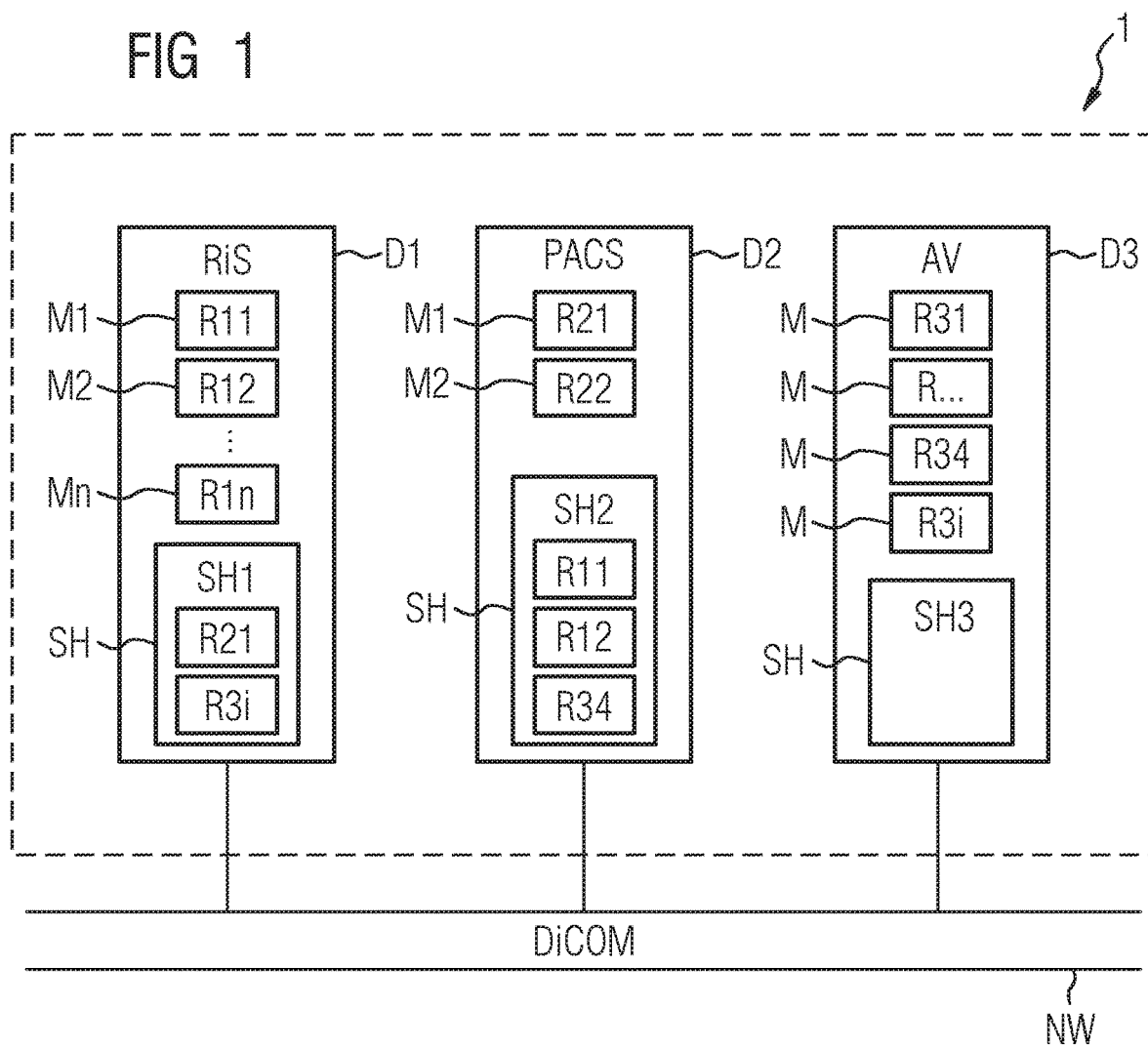
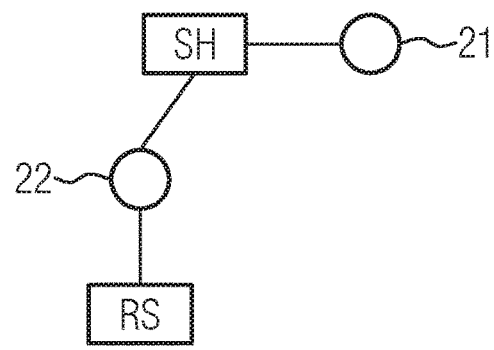

SEMANTIC SHARING OF RESOURCES IN A NETWORK OF MEDICAL DEVICES

PRIORITY STATEMENT

The present application hereby claims priority under 35 U.S.C. § 119 to European patent application number EP 17204310.1 filed Nov. 29, 2017, the entire contents of which are hereby incorporated herein by reference.

FIELD

Embodiments of the invention generally relate to sharing technical resources in a network of medical and/or technical devices, like imaging modalities, advanced visualization systems, post-processing systems, storage and archive devices.

BACKGROUND

Medical devices are typically autonomous. The devices deliver their resources and service according to the intended use. They integrate into the customer environment through domain communication standards such as DICOM and HL7 or through IT standards such as Active Directory protocols like LDAP, Kerberos, DNS etc. Most devices bring their own resources for functions like device configuration or license management etc. These services are intended for local device utilization. Furthermore, devices keep internal state (e.g. logged in user, patient diagnosis processing status, job queue status and contents etc.). This implies that newly bought devices need to be configured manually—very similar to what has been done for other devices before at each customer site. For example, own licenses must be administered for each new device. Also, entry of system configuration data (for example technical device configuration data) needs to be done for each device separately and iteratively in the same way, which is error prone.

Each of the devices in state of the art keeps its own local status isolated from the other devices if there is no central information system (available). For example, patient information is typed in during patient check-in in a first device of a hospital. Later, during examination for example in an MRT apparatus serving as a second device in this example, the same patient information needs to be accessed and typed in anew, because the first and second device are autonomous devices in this decentral scenario.

Thus, in state of the art it is known to configure devices manually. This, however, is error-prone and time consuming. Especially in departmental or enterprise scenarios where a new device is installed which needs to know about all existing devices is a tedious and error-prone endeavor.

If devices were provided by different manufacturers and use different technical platforms it may become difficult to exchange data due to different technical platforms, protocols, interfaces etc.

In state of the art for non-medical appliances and data exchange it is further known to provide a central node, which may act as broker or proxy to exchange device-specific data. However, with these systems it is not possible to consider additional information which is not present in the original message to be transferred. Further, this requires additional hard- and/or software structures to be implemented and therefore has disadvantages.

SUMMARY

At least one embodiment of the present invention provides a solution for making available resources across distributed devices in an efficient manner. Further, resources should be made available without a central infrastructure. Configuration of devices should be automated by making available status information of other network devices automatically. Further, the drawbacks of the state of the art systems as mentioned above shall be reduced or even overcome.

Embodiments of the present invention are directed to a system, a device, a method and a computer program product. Advantageous features and embodiments are mentioned in the claims and in the description.

According to a first embodiment, the invention relates to a decentral sharing system (in the following also shortly referred to as "system") for making available computing resources, including data (like status data, configuration data) and functionality (like services or in the form of applications) on technical or medical devices (which may be provided as network nodes) within a medical network, comprising:

a plurality of distributed (network) devices, which are interconnected by a network, like for example TCP/IP or other internet protocol based networks, which are used to exchange DICOM (Digital Imaging and Communications in Medicine) or HL7 messages and which are registered in the (sharing) system;

wherein each device comprises at least one module communicating via a device-specific interface (or protocol) for providing a specific resource (e.g. a specific functionality or information) locally on the device;

wherein each or selected device(s) is/are provided with a service host for providing local (or own) resources to other remote devices and for accessing foreign resources of at least one remote device.

In a second embodiment, mentioned above, a device is disclosed for usage in a medical network according to the system described before. The device comprises:

at least one module communicating via a device-specific interface for providing at least one resource locally on the device;

a service host for providing the at least one local resource to remote devices and for accessing foreign resources of at least one remote device.

An example embodiment of the invention further relates to a method for decentrally sharing or making available computing resources on devices within a medical network, wherein the method comprises the following steps:

Providing a plurality of resources on distributed devices, which are interconnected by a network (e.g. TCP/IP) and which have been registered in a sharing system;

wherein each of the resources is provided locally on a device and communicates via a device-specific interface in the domain of the device;

Providing local resources to remote devices and mutually accessing foreign resources of at least one remote device without any central control.

In another embodiment, the present invention refers to a tangibility, embodying a program of machine-readable instructions executable by a digital processing apparatus, like a computer, to perform a method for making available local computing resources on other devices within a medical network system and for accessing foreign resources of remote devices. The program may be stored on a computer readable medium.

BRIEF DESCRIPTION OF THE DRAWINGS

FIG. 1 shows a schematic representation of a system for mutual sharing of resources within a medical network in an overview manner.

FIG. 2 shows a schematic representation of a registry abstraction according to an example embodiment of the invention.

DETAILED DESCRIPTION OF THE EXAMPLE EMBODIMENTS

Figure 3:
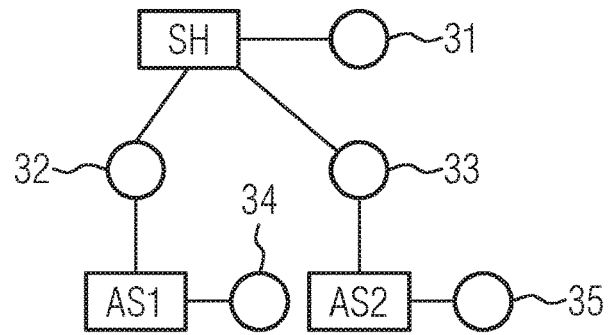
FIG. 3 represents the ability of a service host to dynamically load the own device specific resources and make their existence discoverable for other devices according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to a first embodiment, the invention relates to a decentral sharing system (in the following also shortly referred to as "system") for making available computing resources, including data (like status data, configuration data) and functionality (like services or in the form of applications) on technical or medical devices (which may be provided as network nodes) within a medical network, comprising:

a plurality of distributed (network) devices, which are interconnected by a network, like for example TCP/IP or other internet protocol based networks, which are used to exchange DICOM (Digital Imaging and Communications in Medicine) or HL7 messages and which are registered in the (sharing) system;

wherein each device comprises at least one module communicating via a device-specific interface (or protocol) for providing a specific resource (e.g. a specific functionality or information) locally on the device;

wherein each or selected device(s) is/are provided with a service host for providing local (or own) resources to other remote devices and for accessing foreign resources of at least one remote device.

According to an embodiment, the invention relates to an automatic converter of medical modules (application and data) from a first device to another second device. Thus, the converter or transducer relates to software applications, to hardware applications in physical or virtual form and/or to data. an embodiment of the invention has the advantage that it is not necessary to provide a central node or unit. Even no further computing entities like distributed mediators are necessary. Only, a network infrastructure is necessary and provided which may be used for data exchange and communication (e.g. DICOM uses TCP/IP as underlying network). Further, the system is flexible in that it is possible to include a new device to make its resources available to existing or future devices as soon as the new device with the service host is registered in the semantic resource sharing network. The converter may be employed as a decentral sharing system, as a method, in a medical device or as computer program product. The converter processes matches the resources to be shared on a semantic level, which may comprise to execute the matching on the "content" of the resource, i.e. the technical purpose or its functionality.

For this purpose, an embodiment of the invention suggests to detect messages which are exchanged in the system (from a sending node to a receiving node) in order to expand them with additional data. The additional data may refer to metadata with respect to the message data (e.g. access rights). The metadata may be accessed by the receiving node. It has to be noted, that the additional data, which may be attached or included in the data package needs not to be already existent in the original message. By contrast, it may be added by the sending node. This is possible, because the expansion mechanism, mentioned above is already initiated on the sending node, where additional data may be accessed. Thus, additional data is accessible on the sending node and is used in the semantic resource sharing network.

According to an example embodiment, the resource is adapted to provide data, including status data and configuration data and/or functionality, including services. The service may be directed to different applications and use cases and may for example offer results with respect to certain "questions" or challenges, like for example "who is currently logged into the sharing network system?" or "Is Dr. ABC currently logged in?". Another application of the system is to provide additional data. For example, a patient is examined at a first device and examination and/or patient related data has been measured and/or detected locally. Then, the examination has to be interrupted or suspended for a certain time phase, because another special device is necessary. The patient is accordingly, transferred to another location, where the special device is accessible. There, the data, which has been detected at the first device would no longer be available at the special device according to known state of the art systems. However, with the semantic resource sharing system, the data indeed is made available at the special device by providing data exchange via the module/interface and the service host.

In an embodiment, the resource thus refers to specific services which are available on a remote device. In another second embodiment the resource refers to specific information or data, like technical configuration data or status data of the technical device.

According to another example embodiment, the resource provides a license sharing functionality for making it possible to share the license for an application between different devices. This embodiment distinguishes between different types of licenses. If device-specific licenses are used, a transfer of the license to other devices is not possible due to licensing terms. Then the service host of the device will act correspondingly and will not provide the respective application resource for making it available to other devices. If other licenses are used, then the related application may be shared on other devices as well.

Another example embodiment relates to a configuration sharing functionality. This makes it possible to automatically exchange configuration data and status information between different devices. As an advantage the configuration data which was manually typed in for a first device is accessible and may be used for configuration of a second device, which reduces the risk for typing errors and misconfigurations.

According to another example embodiment, the service host comprises a communication host which serves as standardized or meta-interface and which is adapted to transform device-specific locations and addresses into uniform locations and addresses and vice versa. Thus, all device-specific locations, interfaces and protocols will be standardized, so that they are accessible across the devices. The uniform locations become valid for all devices in the system. It has to be pointed out that no central registry or node is necessary; only a uniform semantic is defined which covers all different device-specific data and interfaces for all devices. An example embodiment of the invention does not use an intermediary. The transformation of device-specific parameters into standardized parameters and vice versa is exclusively executed in the device. Thus, the devices communicate directly without intermediary.

According to another example embodiment, some or all of the devices may be operated with different or even with device specific operating system or firmware. This makes it possible to share functionality and/or data although the devices are provided from different vendors or manufacturers. Also, it is possible to share information although different versions of the same operating system or firmware are used. The operating system relates to the definition of interfaces (like APIs), protocols, parameters. The operating system relates to system software that manages computer hardware and software resources and provides common services for computer programs.

Further, an example embodiment of the invention provides interoperability also for different software states or versions of the same product of the same producer with the same operating system. For example, a first version of a manufacturer of a medical product may use an SQL database, whereas the second version of the same product uses an object-oriented database. Also in this case, the present invention provides data exchange and interoperability.

According to another example embodiment, the service host is configured to select a discovery strategy for detecting remote devices which provide target resources at runtime.

The service host is configured to apply at least one of the following mechanisms as a discovery strategy for detecting an initial set of remote devices with the target resources:

A shared repository or file;

An iterative mechanism which discovers an initial peer (device) and uses the initial peer to discover further peers (devices);

A service locator protocol for discovering an existence, a location within the network, and a configuration of the target resource in the network.

An advantage is to be seen in that according to an example embodiment of the invention this initial list will be extended dynamically. I.e. if a new device is registered in the network and will participate in the resource sharing mechanism, this device allows for mutual exploration with respect to other already registered devices. Thus, it makes available its own resources to be discovered or explored by other devices and may access foreign resources of a remote device or of more than one remote device.

Generally, it is possible to define different sharing rules and conditions for different segments of the network. Thus, different discovery mechanisms are applied in different network segments, so that e.g. for radiology a first discovery mechanism is used, whereas for intensive care a second discovery mechanism is going to be applied.

According to another example embodiment, the service host comprises a discovery interface that allows for mutual exploration of the devices' resources. This has the advantage that foreign resources are discoverable without any central node.

An important technical embodiment of the invention is to be seen in that the (sharing) system is operated completely decentrally and without a central storage or a central node acting as intermediary or broker.

Another important technical embodiment of the invention is, that the service host is dynamically extendable without amending a host process during runtime.

In a second embodiment, a device is disclosed for usage in a medical network according to the system described before. The device comprises:

at least one module communicating via a device-specific interface for providing at least one resource locally on the device;

a service host for providing the at least one local resource to remote devices and for accessing foreign resources of at least one remote device.

An example embodiment of the invention further relates to a method for decentrally sharing or making available computing resources on devices within a medical network, wherein the method comprises the following steps:

Providing a plurality of resources on distributed devices, which are interconnected by a network (e.g. TCP/IP) and which have been registered in a sharing system;

wherein each of the resources is provided locally on a device and communicates via a device-specific interface in the domain of the device;

Providing local resources to remote devices and mutually accessing foreign resources of at least one remote device without any central control.

According to another example embodiment of the method, the local resource locations (addresses) are transformed into uniform locations, which are accessible by all devices. This transformation is executed locally within the device by way of the service host and/or communication host.

According to another example embodiment of the method, the local interfaces (e.g. APIs, application programmable interfaces) are transformed into uniform interfaces, by applying a standardized semantic transformation algorithm. The standardized semantic transformation algorithm is a standardization with respect to interactions (interfaces and protocols) and transferred data in these protocols. Interfaces and protocols are implemented in the DomainService module.

The method of at least one embodiment and in particular the step of providing may be implemented as a computer program and may be provided as a computer program product. The computer program product tangibly embodies a program of machine-readable instructions executable by a digital processing apparatus to perform a method as described before, if the program is executed on the digital processing apparatus. In particular, the execution of the service host may be done via software. Thus, the step of providing local resources to remote devices and mutually accessing foreign resources of at least one remote device without any central control may be implemented in software code.

In another embodiment, the present invention refers to a tangibility, embodying a program of machine-readable instructions executable by a digital processing apparatus, like a computer, to perform a method for making available local computing resources on other devices within a medical network system and for accessing foreign resources of remote devices. The program may be stored on a computer readable medium.

In the following a short definition of terms is given.

The sharing system is a computer system with a plurality of technical or medical devices, which are interconnected via a network for data exchange. The sharing system is decentral. The sharing system is based on semantic compatibility. The sharing system, therefore, is to be construed as a semantic resource sharing network (and the claimed method and device and product as well). This has the technical advantage that no central unit, node, broker, proxy or entity is necessary. Nor is it necessary to provide a local entity with a central administration or orchestration function. The system is a computer system and provides automatic data processing.

The network is a computer network which interconnects medical, technical and other computing nodes, like imaging modalities, visualization systems, post processing systems, storage systems like PACS (Picture Archiving and Communications in Medicine) and information systems, like RIS (Radiology Information System).

The term "resources" is to be construed as technical resources, like resources for providing functionality and/or data. Resources may provide services and may be implemented in software. The software may be provided in technical modules, for example hardware modules, in the devices. Resources may be provided in a virtual form, like e.g. virtual hardware resources. Resources may, for example, relate to configuration resources (automatic configuration of technical devices and/or providing configuration data from related but remote devices for automatic configuration) and/or to licensing resources or to processing resources, including visualization techniques, storage capacities. Resources may also relate to information or data. Data (e.g. patient data) may be provided locally on a first device (e.g. check-in or registration computer) and may be prepared for being shared with other second devices, which are operated with a different operating system or communication protocol (e.g. imaging modality for reading in patient data automatically form first device).

A device which is connected to the network may choose to be registered in the sharing service according to an embodiment of the invention. In this case, the device will register to the system in order to share its resources with other devices and to access and/or use resources from other devices. This step, however, is optional and may be reversed again. With other words, the participation in the sharing system may be activated and deactivated at any time after registration and also during runtime of the system. This is especially important, if for example a device is adapted to detect or provide PHI information (Protected health information) which needs to be processed in a very restrictive manner. In this case, the device may opt-out of the sharing system in order to make sure that the PHI information will not be accessed from other devices. Another option may be, to define rules, that provide an access and distribution scheme how to share the PHI information, e.g. only to dedicated and selected devices in a dedicated time phase.

The devices may be provided in a set or group of devices within a domain. A domain may be defined on the basis of semantic compatibility of the offered domain services. Thus, the services in such a group or set serve the same or similar semantic resources. Domain services are shared between (different) devices, platforms and operating systems.

The devices are distributed and connected via a network, e.g. wirelessly like TCP/IP or any other network.

The devices are equipped with a module. The module is for providing at least one resource. For example, the module may be a processor and the resource may be a visualization functionality. The modules are device-specific and operated in a specific set of devices or platform or operating system. The devices modules use device-specific interfaces for internal communication. The module serves for providing at least one resource locally on the device. Based on semantic compatibility, the sharing system makes this resource available to other devices which may be within another domain and which may use another operating and communication system, i.e. another protocol.

The service host is device-specific. The service host provides sharing functionality. It is for providing local resources to remote devices and for accessing foreign resources of at least one remote device by automatically adapting different operating systems and different local communications systems (the device local protocols and interfaces for accessing the respective resource). Outside of the device, the shared domain services are used, which are accessed by the interacting devices uniformly.

The operating system is to be construed as system for operating the device on behalf of communication and data exchange. The operating system, in particular, refers to the definition of communication interfaces and protocols. Further the operating system controls the device internal addresses for assessing a respective resource and/or a module providing the resource (if a functionality). The operating system may, thus, be construed in particular as communication protocol. The communication protocol is a system of rules that allow two or more modules of the device to transmit information via any kind of variation of a physical quantity. The communication protocol may be adapted for local as well as for shared access. The protocol defines the rules syntax, semantics and synchronization of communication and possible error recovery methods. Protocols may be implemented by hardware, software, or a combination of both.

The communication host serves as meta-interface and is adapted to transform device-specific units and parameters (e.g. locations or addresses of the modules/resources) into uniform units and parameters with a central sematic across all devices having different device-specific units, parameters and vice versa. "Vice versa" in this context means, that uniform units according to the central and standardized semantic of the meta-interface are in turn transformed into the device-specific units of the respective requesting device. The communication host may, in particular, be adapted to execute the standardized semantic transformation algorithm.

FIG. 1 shows an overview of a system 1 for sharing resources across a plurality of networked devices D. The devices D are part of a medical system, like a clinical domain.

The devices D are interconnected by a network NW (for example TCP/IP-based protocols), which is used to exchange e.g. DICOM or HL7 messages or others.

The devices D are typically distributed entities and are located at remote locations. The devices D are normally operated with different operating conditions, because they may stem from different vendors. Thus, a first device D1 may be operated locally or internally with a first communication protocol and a second device D2 may be operated with a local or internal second communication protocol, wherein the both protocols typically are not compatible with each other and have other semantics.

A device D, like for example an imaging device like a MRT modality or a CT modality or an advanced visualization device typically is a complex electronic apparatus, which comprises of a plurality of modules M. The modules M are adapted to execute at least one specific functionality or service (e.g. providing configuration data, post processing image data, providing patient data etc.). The modules M may be further adapted to provide virtual resources R, for example virtual hardware resources, like storage capacity. The modules M interact within the device via a device specific interface, API. The device comprises two categories of resources R:
  1. Local resources, which are provided by the device-internal modules M and thus are "own" resources and
  2. Foreign resources, which are provided via a Service Host SH from remote devices and are not provided locally.

For this reason, every device D, which has registered in the sharing system 1, comprises a service host SH. This may be a software applet or module, which may be employed also during runtime and operation of the device. The service host SH is device specific and is adapted to provide resources to foreign devices and for sharing its own resources. Via the service host SH it is possible for a remote system to access local resources of the system on which the service host is implemented.

In the schematic example of FIG. 1, the service host SH1 of the first device D1 provides resources R21 and R3i of the second and third foreign device D2 and D3, whereas the service host SH2 of the second device D2 provides resources R11, R12 and R34 of the first and third foreign device D1 and D3 and so on.

In a preparation phase the devices may register or check-in to the sharing system 1 in order to share their resources R with other devices D. In this phase the service host SH will be installed on the respective device D.

In a particular example embodiment of the invention, the sharing functionality may be activated and deactivated due to pre-definable rules and conditions (e.g. transmission of PHI information, special clinical requirements etc.) once being registered.

Due to the fact that the resources on the different devices D are not compatible, they first have to be prepared (transformed) for being shared with other devices D. This is done by a service host SH by way of applying the standardized semantic transformation algorithm.

In general, an example embodiment of the invention enables information and resource sharing between devices D being operated with different local systems, interfaces and/or protocols.

An example embodiment of the invention relates to information and resource sharing between medical devices D across different products and product versions without requiring a central service. This is achieved by the device specific service host SH, as mentioned above.

The service host SH is the runtime environment in which the communication host is integral part of and by which the requested domain web services may be discovered (for foreign devices). The service host SH loads the respective requested (additional) domain (web) services and registers them locally at the communication host. Only with this feature, the additional services become discoverable by other devices.

The service host SH may be adapted to execute the following steps:
Starting a communication host on each device D that supports mutual discovery of other communication host instances in the network NW without violation of security policies in the environment.

The service host dynamically loads additional webservices exposing domain specific application programmable interfaces, APIs.

Each webservice provides a plug-in interface through which a product (-version) specific implementation logic of the webservice can be loaded. Each web service comprises three parts: 1) a communication façade, which in the figures is also named as Domain service; 2) a plug-in adapter as a domain service host and 3) the core device-specific implementation as Domain service implementation.

A communication host can be understood as a subsystem of the service host SH. It is responsible for data exchange and communication across the devices D. The Communication host is responsible for running a discovery protocol and for making the locally registered domain services discoverable. The service host comprises the communication host an integral part. The service host loads the requested or desired domain services and registers them at the communication host.

Service hosts SH can be configured to use different discovery strategies—depending on the customer site specific conditions. Depending on the capabilities of the respective medical device D different domain services can be exposed as resources R. Based on the resource sharing patterns logged during operations, workflow optimizations and consulting services can be offered, enabling customers to work more efficiently with their systems. E.g. by observing how many license sharing requests are served across the systems at one site, it can be detected whether additional licenses are needed or should be migrated over to another system. This yields to qualified and quantified improvement proposals.

Each communication host exposes a well-known standardized discovery interface that allows mutual exploration of the identified target system capabilities. Through this interface a client device D can:

1) Obtain the identity of the target system.

The identity can be used for unique identification of the peer system. Examples of unique identities could be product serial number including product name (assuming that within each product the serial numbers in the installed base are unique). Knowing the peer identity with which the interaction potentially takes place can be used for deciding on whether to interact with that device D or not.

2) Ask the peer about known other peers

By that additional peers can be discovered that were previously not known to the request initiating device D. A list of endpoint addresses is returned that can be used to discover more peers.

3) Ask the device for the list of additionally provided webservices available at the target system Through this query, a client becomes aware of whether the device D does support configuration exchange service, license sharing service, protocol sharing service etc.

4) Obtain the webservice address for specific additionally provided webservice

Using this address a client device D is capable of requesting the specific service (resource R) from a remote device D.

After starting the system 1 for the first time, an initial list of devices D, in the following also named 'peers' has to be defined, which may serve as communication entity. Peers make a portion of their resources R, such as processing power, disk storage or network bandwidth, directly available to other network participants or registered devices D respectively, without the need for central coordination by servers or stable hosts. Peers may act as both suppliers and consumers of resources R, in contrast to the traditional client-server model in which the consumption and supply of resources R is divided.

The initial list of peers can be obtained using different mechanisms:

1) A shared repository, in which peers register themselves and can therefore be looked-up as well (e.g. shared file, cloud service, etc.).
2) A well-known peer is passed at start-up time to the communication host, from which the host then obtains further peers after start-up iteratively or sequentially.
3) Using a Service Locator Protocol, for example defined by IETF, when supported by the network infrastructure.
4) A Service Technician inserts a memory stick at a known peer, exports repository information to the stick and inserts the stick in the new device, which obtains the initial set of peers then by reading the exported repository information.

The applicable discovery strategy at a customer site on a device D can be decided at runtime and is independent from the additional domain services.

Being able to dynamically discover the network of devices D and make use of their provided resources and services will cover enterprise and departmental scenarios described above. One example scenario may relate to Siemens Healthineers teamplay. Siemens Healthineers teamplay is a departmental or enterprise portal capable of collecting data from known devices D and presenting views on this data to customers (other client devices D). Data collection is done by the so-called Siemens Healthineers teamplay receiver, which queries the relevant data from connected devices. In this example, the discovery strategy will enable Siemens Healthineers teamplay to locate existing Siemens Healthineers products and devices D at time of installation, reducing the task of the clinical administrator to manually configure those devices D and their DICOM entities in Siemens Healthineers teamplay receiver.

Each additional service (which will be provided as a resource R) must expose a service specific interface that is standardized across all devices D that want to support this specific service and are therefore registered in the system 1. Thus, there is a central definition for such services and resources R with a clear description of the service semantics, the communication protocols, the API protocols and the meaning of the parameters to ensure semantic interoperability between different devices D, like products and interested clients.

In the following an example for a license sharing service interface will be described.

Bool LicenseExistsForSharing(string licenseName)

Enables a client device D to detect whether a peer implementing the license sharing service is capable of sharing the license with the specified name String TryCheckoutlicense(string licenseName, int LicenseLeaseRenewalTime, string identity)

Request to check-out the specified license and declare that while the client device D holds the license the lease is periodically renewed in specified time. The requesting client device D submits its identity to make sure that client usage can be tracked to specific clients. If the client is not known or the <LicenseLeaseRenewalTime> is considered too long, the service might reject the check-out attempt. If the client fails to renew or release the lease in due time, the service might auto-release the license and refuse further license check-out attempts by that client.

String RenewLicenseLease (string grantedLease, string identity)

Request for keeping the license checked-out for the client with specified identity.

Bool ReleaseLicense (string grantedLease, string identity)

Client with specified identity releases the granted license and makes it available again for other client's usage.

The protocol between client and service is obvious, but the implementation to check-out the real license is product-specific. Some products might utilize FlexLM as license management others might have implemented their own license management. Usually also the license names are different between product lines. Therefore, the logic behind the web service interface shown above needs to be implemented separate for each product and/or product line.

This logic needs for one aspect a translation from product specific parameters, like license names to normalized parameters, like license scheme (agreed across all product lines) and the other way around before checking out a remote license (via the webservice API) or checking out a local license on behalf of a remote webservice call.

The list of exposed additional service resources R can be decided at runtime.

The product specific implementation of the additional service resources R can be decided at runtime as well.

A second example embodiment of the present invention relates to a configuration service resource R. Here, configuration data, relating to the setting of technical parameters of a first apparatus or device D1 should be shared and automatically made available for configuration of a second device D2 without an intermediate computing node.

This is especially important, because for medical devices D there is no standard as to how these devices D persist their configuration data. Configuration data may be stored in a registry in the operating system or in a database. Further, the syntax for the configuration data is not standardized and may thus differ from device Di to device Dj. If, for example, a first modality D1 has configured a new printer for printing image data and has aggregated a set of actual configuration data for this printer, then, these configuration data may be automatically shared with another second device D2, for which the printer should also be registered.

A device D may decide to participate in the sharing system 1 or not. If yes, in a preparation phase, a rendezvouz-protocol is applied between the devices in order to exchange mutual information. In particular, the address or location of the resources R have to be provided as well as the capabilities of the respective device D and the interfaces and protocols (port number etc.). In particular, all information has to be provided which is needed to provide the identity of the resource R, to transfer device-specific locations/addresses into standardized locations/addresses according to a standardized semantic.

FIG. 1 depicts a typical customer system topology in a schematic manner. In general, in such a typical clinical scenario, modalities, like MR or CT scanners, retrieve a modality worklist from the Radiology Information Systems (RIS) and send acquisition results to Picture Archiving and Communication System (PACS) and Advanced Visualisation Systems (AV). AV-Systems also retrieve modality worklists from RIS to know in advance about patients to be examined and expect acquisition data to arrive. Furthermore, AV systems retrieve prior data for patients from PACS (if needed) and send post-processing results back to PACS.

As the picture shows, many of the topology configuration values 'relevant for combination, "Modality 1, AV system 1" are also relevant for combination of "Modality 2, AV System 2". An example embodiment of the invention enables all discoverable devices D to explore the configuration settings of the other peers or devices D respectively and thus reduce the amount of manual configuration needed (including elimination of mistyped information).

In general, all registered devices D may provide their resources R for sharing and may use foreign resources R. Thus, the discovery network topology is such that there are end to end connections to each of the registered devices D. The context of the situation may e.g. relate to the fact that each registered device D becomes aware of the other discoverable devices D in the network NW (each device D in the above network knows about its four peers).

Being able to discover the peers, each device D is also capable to learn about the provided resources R from each peer. That might e.g. allow the two modality peers to share protocol information while at the same time the AV systems might start sharing application licenses or computing resources R at runtime.

FIG. 2 depicts the registry abstraction that is used to record the identified peers. An implementation for a registry service RS goes along with a selected discovery service 21 and can be decided individually for different customer site devices D.

FIG. 3 shows the ability of the service host SH to dynamically load those domain services as added service AS1, AS2 (like licensing, configuration access, protocol access, etc.) and make their existence available through an IDiscoveryService interface 31. The service host SH comprises in the example embodiment shown in FIG. 3 two plug-ins, a first DeviceServiceProvider 32 for the first service resource AS1 and a second DeviceServiceProvider 33 for the second service resource AS2. The first service resource AS1 is related to a first DomainService 34 and the second service resource AS2 is related to a second DomainService 35—

Figure 4:
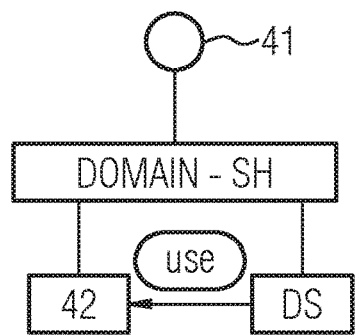
FIG. 4 represents a schematic representation of a domain service container with sub-units in a structural manner.

FIG. 4 finally shows the structure of an additional service resource R consisting of the domain service container DOMAIN-SH which hosts the domain service specific webservice interface, a DomainService DS and dynamically loads the device specific domain service implementation 42. Reference numeral 41 refers to a DeviceServiceProvider.

The interface/DeviceServiceProvider needs to be implemented by each domain service. By the DeviceServiceProvider, the service host may load the specific domain service at runtime and to control its lifecycle:

```
public interface ISmartDeviceServiceProvider
{
    bool Init( );
    string GetServiceName( );
    string GetBaseAddress( );
    bool StartService( );
    bool Shutdown( );
}
```

At least one example embodiment of the present invention have several advantages.

It provides for a flexible location of (smart) devices D in a customer environment network NW. The initial discovery protocol is configurable and can be adapted to the needs of the customer environment. By using the IDiscovery interface of each device D enables clients (other devices D) to know about the capabilities and additional service resources R provided to the network by this particular device D. Further, building up a network of interoperable domain services is possible without the need for a central infrastructure. Also, the invention helps reducing implementation efforts of participating devices D mostly to the local implementation of domain services. Finally, products are enhanced by making flexible use of the network of provided service resources R.

Figure 5:
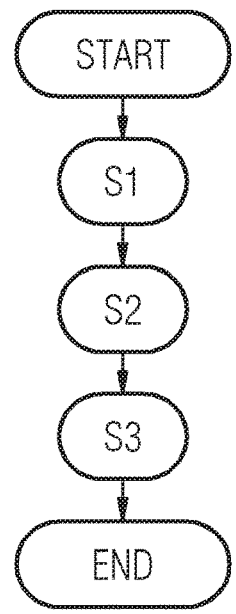
FIG. 5 is a flow chart of a method according to an example embodiment of the present invention.

FIG. 5 shows a flow chart according to an example embodiment of the invention. After having started the method, a plurality of resources R on distributed and registered devices D are provided in step S1, which are interconnected by a network (DICOM), wherein each of the resources R is provided locally on the respective device D and communicates via a device-specific interface. In step S2 local resources R are provided to remote devices and mutually in step S3 foreign resources R are accessed and may be used locally of at least one remote device without any central control.

Figure 6:
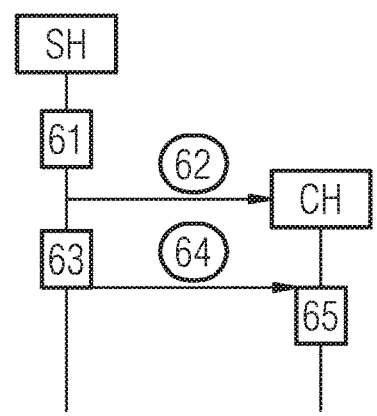
FIG. 6 is an interaction and sequence diagram, showing interactions between a service host and a communication host.

FIG. 6 shows the communication between the service host SH and the communication host, which is depicted in FIG. 6 with reference numeral CH. In a first step 61, the service host SH loads all configured web services. Then, in step 62 it instantiates the communication host CH. In step 63 lifecycle policies are applied on the service host SH by defining which of the services should be made discoverable and accessible at what time and for which nodes or devices. At 64 web services are registered. At 65, the services are inserted into the local registry. Loaded domain web services will only become discoverable if the service host SH already has initialized these services. The process of loading may be executed dynamically.

Figure 7:
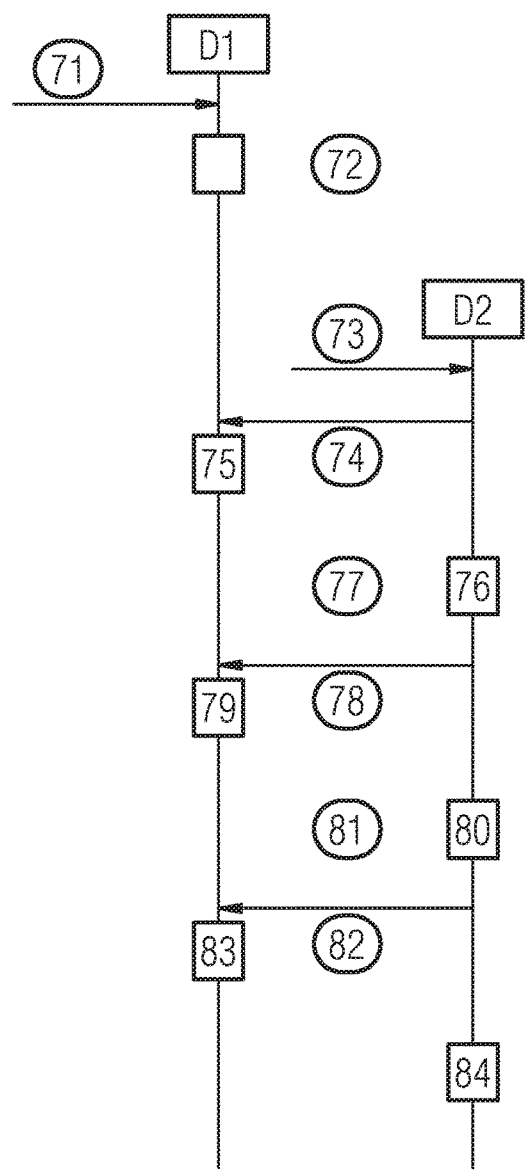
FIG. 7 is a flow chart of a data exchange for a rendezvous between two medical devices according to an example embodiment of the present invention.

FIG. 7 shows the rendezvous protocol of two devices D1 and D2. At 71 the service technician configures the device D1 (e.g. a RIS, Radiology Information System) manually. In 72, the local system of D1 persists configuration data locally. In step 73, the service technician initiates the discovery protocol on the second device D2. In interaction 74 a challenge is issued for getting the identity with GetIdentity/My Identity. In 75, the invoking identity is verified and the own identity of the first device D1 is returned. The device's identity may for example comprise the following identity items: serial number of the device, the type of the device, the software version and the MAC address of the network interfaces. The list of available peers is updated. In 76, the returned identity is verified on the second device D2 and the list of available peers is updated. Reference numeral 77 should indicate that at this time, both systems D1, D2 know about the existence of the other (rendezvous). In 78, a function 'GetKnownPeers' is executed. In 79, all known peers are returned to the caller. In 80, this list of known peers is updated. Reference numeral 81 should indicate that at this time, both systems D1, D2 have the same list of known peers. At 82, a function 'GetProviderServicer' is executed. If, for example, D1 supports a configuration service, then D2 may access and use this service from the local configuration software of D2. In 83, all the supported services are returned by the peer to the caller and in step 84 the list of supported services for given peer is updated at D2.

The resources R may serve different functions or functionalities, like license management or configuration of the device. License generation, administration and distribution add overhead per device as well on producer side if executed for each time anew. Furthermore, licenses per device limit the usage of the license on specific devices rather than making them available for all devices of a specific type in customer environment. With the service host SH according to the invention, these disadvantages can be overcome.

Figure 8:
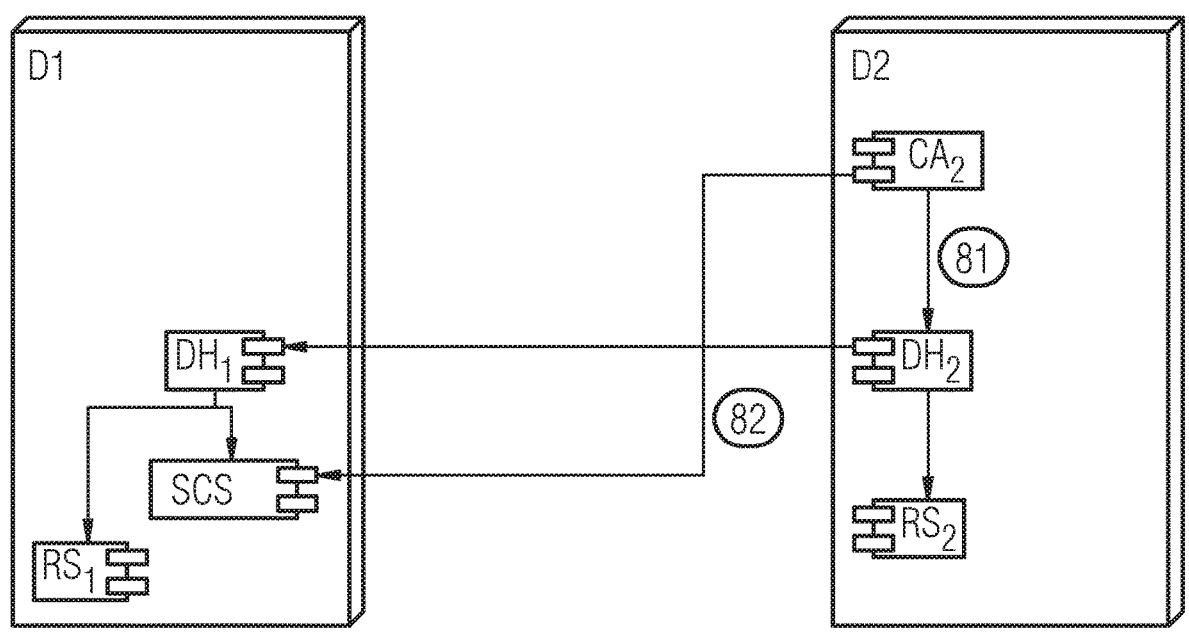
FIG. 8 shows a use case for sharing system configuration services according to an example embodiment of the invention.

FIG. 8 shows a possible embodiment of the invention by applying the sharing system for a configuration service. D1 and D2 both comprise a device host $DH_1$, $DH_2$, wherein each of them has stored information about the discovered systems and resources available thereon in the respective registry services $RS_1$, $RS_2$. D1 provides a system configuration service SCS, which was discovered by D2.

Thus, in the registry service $RS_2$ of D2 there is stored the identity of D1 and its resource—in this example—for providing a system configuration service SCS, which would not be available without sharing on D1. Reversely, on D1 a system configuration service SCS is available, which has been discovered by D2. Thus, in the registry service $RS_2$ of D2 the device D1 and its resources are prepared for being offered. At 81, the local system configuration application $CA_2$ of device D2, which is used for configuring device D2, requests the local device host $DH_2$ to provide systems, which provide system configuration services SCS and receives in reply to this request in step 82 the address of system configuration service SCS of D1. With this information, the configuration application $CA_2$ can access the system configuration services of device D1 for receiving data therefrom.

In an example embodiment the data received from another (foreign) device will first be visualized and verified before they will be used. This enhances security.

If more than one system configuration service from different devices D3, D4, D5 would be available, the system configuration application could preferably access a decision logic, which is adapted to implement rules for deciding which system configuration from which device should be used. Here, it could be defined that if one of the devices is currently not in mobile data connection or is turned off, it should not be used. If both devices D1, D2 are of the same type, then a message could be prepared for offering to also use and transfer the application configurations so that the user will have the same look and feel.

The process of finding another device (rendezvous protocol) may be executed by applying a service locater protocol SLP. After complete execution of the discovery procedure, the respective devices D1, D2 mutually know, which of the services of the respective other (foreign) device are offered.

For implementation of a domain service the conventions, definitions and rules of each local device D are transformed into date structures and operations which are valid between all the devices. For example, on the first device D1, e.g. a computer tomographic apparatus, the data are stored in a relational data-base with a set of attributes, comprising, title, role, address etc. For detecting configuration data on this first device D1 for a second device D2 (e.g. PACS), a issues a query for—in this example—a system configuration service SCS needs to be executed on the database with respect to the table, mentioned above.

The systematic transformation algorithm defines a syntax with which configuration data may be exchanged between the registered devices of the system 1 by maintaining the (may be different) local semantics. In the following there is given an xml scheme by way of example:

```
<xs:schema attributeFormDefault="unqualified" element-
FormDefault="qualified"
xmlns:xs="http://www.w3.org/2001/XMLSchema">
    <xs:element name="DICOM_Device">
        <xs:complexType>
            <xs:sequence>
                <xs:element name="AE_Title">
                    <xs:complexType>
                        <xs:simpleContent>
                            <xs:extension base="xs:string">
<xs:attribute name="Role" type="xs:string" use="required" />
                            </xs:extension>
                        </xs:simpleContent>
                    </xs:complexType>
                </xs:element>
                <xs:element name="Host">
                    <xs:complexType>
                        <xs:sequence>
                            <xs:element name="IP_Address" type="xs:string"
/>
                            <xs:element name="Port" type="xs:unsignedByte"
/>
                        </xs:sequence>
                    </xs:complexType>
                </xs:element>
                <xs:element name="TransferSyntax" type="xs:string" />
            </xs:sequence>
            <xs:attribute name="LocalName" type="xs:string"
use="required" />
        </xs:complexType>
    </xs:element>
</xs:schema>.
```

Besides this transformation scheme, a description will be provided for the developer of a domain service for generating his messages in compatibility to the system (this refers to a design and implementation phase). During runtime, if the devices exchange (e.g. configuration) data, the information, provided in the interaction/dialog process may be used by the service technician to help him to decide whether or not the transformation is executed correctly, so that the service technicians may verify the same.

If one would apply the above scheme to the example given above for requesting the configuration of the second device D2, an xml string will be returned as result:

```
<DICOM_Device LocalName="Dev1">
    <AE_Title Role="Image Archive">OurArchive</AE_Title>
    <Host>
        <IP_Address>197.067.233. 044</IP_Address>
        <Port>104</Port>
    </Host>
    <TransferSyntax> 1.2.840.10008.1.2</TransferSyntax>
</DICOM_Device>.
```

When requesting the first device D1, the following result string will be returned:

```
<DICOM_Device LocalName="Store1">
    <AE_Title Role="Image Archive">OurArchive</AE_Title>
    <IP_Address>197.067.233. 044</IP_Address>
        <Port>104</Port>
    </Host>
    <TransferSyntax> 1.2.840.10008.1.2</TransferSyntax>
</DICOM_Device>.
```

The transformation algorithm is a normative description for each compatible domain service, how to transfer the local resource information into a semantic equivalent information (data structure) which will be understood by all (foreign) compatible devices.

The transformation will have the following result:

Provided that, a first device D1 requests result data of a foreign compatible second device D2, then the request of D1 is generated in a local language of D1 and is transformed into a uniform language (understandable by all devices) and transferred to the second device D2. After receipt on D2, the string in the uniform language is transferred again into the local language of D2 to be executed thereon. After providing the result in the local language, the local result string is transformed again in the uniform language to be transferred to the first device D1 where it will be transformed again in the local language of D1 to be processed locally on D1. The string may be provided in an xml format.

A further example for a scenario where the invention could be used is collecting data from all devices. Keeping the list of devices manually in synchronisation with continuous modifications in the topology according to state of the art is error-prone. Moving internal state from one device to another device is typically done by re-typing the information manually. The invention, however, does not necessitate a manual re-typing, because data may be automatically transferred directly from the first to a second device by using the service host SH as a normalized interface which is valid for all different devices. Example: A patient has been registered at one scanner device D which uses protocol P1 and the data needs to be accessed on a second device D2 which uses protocol P2 by automatic transfer of the service host SH.

While the current invention has been described in relation to its example embodiments, it is to be understood that this description is for illustrative purposes only. For example, the device D may be a medical apparatus or another technical apparatus, for example being administered as fleet management. For the person skilled in the art it is clear that the invention may also be used for other resources R or services besides configuration and licensing. For example, the resource R may also relate to providing virtual storage capacity or processor capacity. Accordingly, it is intended that the invention be limited only by the scope of the claims appended hereto.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A decentralized sharing system for sharing computing resources within a medical network, the decentralized sharing system comprising:
   a plurality of distributed devices, registered in the decentralized sharing system and interconnected within the medical network, each respective device, among the plurality of distributed devices, including at least one processor and having at least one mode to communicate via a device-specific interface to locally provide at least one resource on the respective device; wherein
      each respective device is provided with a device-specific service host to provide at least one local resource to remote devices and to access at least one foreign resource of at least one remote device among the remote devices;
      the device-specific service host includes a communication host to serve as a meta-interface, and
      the device-specific service host is configured to transform device-specific locations into uniform locations with a central semantic for the plurality of distributed devices.

2. The decentralized sharing system of claim 1, wherein the at least one resource is configured to provide at least one of data or functionality, the data including status data and configuration data, and the functionality, including services.

3. The decentralized sharing system of claim 2, wherein the at least one resource provides a license sharing functionality.

4. The decentralized sharing system of claim 2, wherein the at least one resource provides a configuration sharing functionality.

5. The decentralized sharing system of claim 1, wherein the at least one resource provides a license sharing functionality.

6. The decentralized sharing system of claim 1, wherein the at least one resource provides a configuration sharing functionality.

7. The decentralized sharing system of claim 1, wherein each of the plurality of distributed devices is operable with a device-specific operating system, which differs between at least two of the plurality of distributed devices.

8. The decentralized sharing system of claim 1, wherein the device-specific service host is configured to apply, as a discovery strategy for detecting an initial set of remote devices with target resources, at least one of:
   a shared repository;
   an iterative mechanism to discover an initial peer and use the initial peer to discover further peers; or
   a service locator protocol to discover an existence, a location within the medical network, and a configuration of the target resource in the medical network.

9. The decentralized sharing system of claim 1, wherein the device-specific service host includes a discovery interface to allow for mutual exploration of resources of the plurality of distributed devices.

10. The decentralized sharing system of claim 1, wherein the decentralized sharing system is completely decentralized and without a central storage or a central node acting as a broker.

11. A decentralized sharing for sharing computing resources within a medical network, the decentralized sharing system comprising:
   a plurality of distributed devices registered in the decentralized sharing system and interconnected within the medical network, each respective device, among the plurality of distributed devices, including at least one processor and having at least one mode to communicate via a device-specific interface to locally provide at least one resource on the respective device; wherein
      each respective device is provided with a device-specific service host to provide at least one local resource to remote devices and to access at least one foreign resource of at least one remote device among the remote devices, and
      the device-specific service host is configured to select a discovery strategy for detecting remote devices with target resources at runtime.

12. The decentralized sharing system of claim 11, wherein the device-specific service host includes a communication host configured to serve as a meta-interface, and is configured to transform device-specific locations into uniform locations with a central semantic for the plurality of distributed devices.

13. A method for sharing computing resources across a plurality of devices within a medical network system, the method comprising:
   providing a plurality of resources on distributed and registered devices interconnected by a network, wherein
      each of the plurality of resources is provided locally on at least one device among the plurality of devices, and
      each of the plurality of resources communicates via a device-specific interface;

providing local resources to remote devices among the plurality of devices;

transforming local resource locations into uniform locations accessible by all registered devices among the plurality of devices; and mutually accessing resources of at least one remote device, among the plurality of devices, without central control.

14. The method of claim 13, further comprising:

transforming local interfaces into uniform interfaces by applying a standardized semantic transformation algorithm.

15. A non-transitory machine-readable medium storing a program of machine-readable instructions, executable by a digital processing apparatus, to perform the method of claim 13 upon the program of machine-readable instructions being executed on the digital processing apparatus.

16. A method for sharing computing resources across a plurality of devices within a medical network system, the method comprising:

providing a plurality of resources on distributed and registered devices interconnected by a network, wherein each of the plurality of resources is provided locally on at least one device among the plurality of devices, and each of the plurality of resources communicates via a device-specific interface;

providing local resources to remote devices among the plurality of devices;

transforming local interfaces into uniform interfaces by applying a standardized semantic transformation algorithm; and mutually accessing resources of at least one remote device, among the plurality of devices, without central control.

17. A non-transitory computer program product tangibly embodying a program of machine-readable instructions, the program of machine-readable instructions executable by a digital processing apparatus to perform the method of claim 16 upon the program of machine-readable instructions being executed on the digital processing apparatus.

* * * * *